United States Patent [19]
Afriat et al.

[11] Patent Number: 6,149,900
[45] Date of Patent: Nov. 21, 2000

[54] STABLE W/O/W EMULSION AND ITS USE AS COSMETIC AND/OR DERMATOLOGICAL COMPOSITION

[75] Inventors: Isabelle Afriat, Paris; Florence Chanvin, Soisy/S/Seine; Carole Guiramand, Linas, all of France

[73] Assignee: L'Oréal S.A., Paris, France

[21] Appl. No.: 09/166,125

[22] Filed: Oct. 5, 1998

[30] Foreign Application Priority Data

Oct. 3, 1997 [FR] France ................... 97 12364

[51] Int. Cl.⁷ .................. A61K 31/74; A61K 7/00
[52] U.S. Cl. .................. 424/78.03; 424/401
[58] Field of Search .................. 424/78.03, 401

[56] References Cited

U.S. PATENT DOCUMENTS 5,567,426  10/1996  Nadaud et al. .

FOREIGN PATENT DOCUMENTS 0 750 899A2  1/1997  European Pat. Off. .
0 779 071A1  6/1997  European Pat. Off. .
0 832 645A1  4/1998  European Pat. Off. .

*Primary Examiner*—Carlos A. Azpuru
*Attorney, Agent, or Firm*—Oblon, Spivak, McClelland, Maier & Neustadt, PC.

[57] ABSTRACT

A composition in the form of a water/oil/water triple emulsion comprising an outer aqueous phase and an oily phase constituting, with an inner aqueous phase, a W/O primary emulsion, the outer aqueous phase comprising, in combination, an emulsifying copolymer of carboxylic acid with a fatty chain, and a crosslinked poly (acrylamidomethylpropane-sulfonic acid). The emulsion remains stable, even in the presence of an acidic active agent, and is particularly appropriate as vehicle for water-sensitive and/or oxygen-sensitive active agents, in particular in a cosmetic or dermatological composition. The active agent can be, in particular, a vitamin, such as ascorbic acid or retinol, an enzyme and an α- or β-hydroxy acid. The emulsion obtained can constitute, in particular, a composition for cleaning and/or treating and/or protecting the skin and/or mucous membranes and/or keratinous fibers.

28 Claims, No Drawings

STABLE W/O/W EMULSION AND ITS USE AS COSMETIC AND/OR DERMATOLOGICAL COMPOSITION

BACKGROUND OF THE INVENTION

1. Field of the Invention

The present invention relates to a composition which is provided in the form of a W/O/W triple emulsion and to its applications in the cosmetic and dermatological fields, in particular for the controlled release of active agent, more particularly of water-sensitive and/or oxygen-sensitive active agent and of acidic active agents, in particular for the purpose of cleaning and/or treating and/or protecting the skin and/or mucous membranes and/or keratinous fibers.

2. Background of the Invention

It is known to introduce active agents into cosmetic and/or dermatological compositions for the purpose of contributing specific treatments to the skin, for example for combating drying, ageing or pigmentation of the skin, for treating acne or certain skin diseases (eczema, psoriasis), for combating excess weight, for promoting restructuring of the skin or its cell renewal, or for coloring the skin.

For example, ascorbic acid (or vitamin C) is known to stimulate the growth of the connective tissue and in particular that of collagen. It also makes it possible to strengthen the defenses of cutaneous tissue against external attacks, such as ultraviolet radiation or pollution. Ascorbic acid is also used for removing blotches and pigmentation of the skin and also for promoting healing of the skin.

In addition, it is known that the application of hydroxy acids to the skin makes it possible in particular to combat cutaneous ageing and certain disorders of the skin, such as acne.

Furthermore, triple emulsions are known to be potentially advantageous in the controlled release of active agents. In particular, they make it possible to protect sensitive active agents against external agents which are harmful to the stability of these active agents, such as water or oxygen. Water/oil/water (W/O/W) emulsions are particularly advantageous because the inner and outer aqueous phases are separated by an oily layer. An active agent encapsulated in the inner phase can thus be maintained outside the outer phase (see article by Dahmer Tagawa, 19th IFSCC Congress, Sydney, 1996). Thus, EP-A-779,071 discloses a W/O/W emulsion containing a water-sensitive active agent.

Unfortunately, certain active agents and in particular acidic active agents, because of their acidity, destabilize the triple emulsions containing them, in particular when the outer aqueous phase is gelled. This lack of stability is reflected by a phase separation and/or the production of a simple O/W emulsion instead of a triple emulsion.

Thus, the need remains for a stable W/O/W emulsion capable of containing acidic cosmetic and/or dermatological active agents.

SUMMARY OF THE INVENTION

The inventors now unexpectedly found a combination of polymers which is suitable for gelling the outer aqueous phase of the triple emulsion and which makes it possible to obtain a water/oil/water (W/O/W) triple emulsion which is stable even in the presence of acidic active agents.

Accordingly, the present invention provides a water/oil/water triple emulsion comprising a gelled outer aqueous phase and an oily phase constituting, with an inner aqueous phase, a water/oil primary emulsion, where the oily phase comprises an emulsifier chosen from alkyl dimethicone copolyols and dimethicone copolyols, and the outer aqueous phase comprises:

1) at least one emulsifying copolymer composed to a major extent of a monoolefinically unsaturated $C_3$–$C_6$ carboxylic acid monomer or of its anhydride and to a minor extent of an acrylic acid fatty ester monomer, and
2) at least one crosslinked poly(acrylamidomethyl-propanesulfonic acid) comprising, distributed randomly:
   a) from 90 to 99.9% by weight of units of following general formula (III):

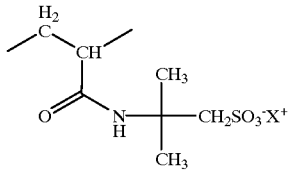

where $X^+$ denotes a cation or a mixture of cations,
   b) from 0.01 to 10% by weight of crosslinking units originating from at least one monomer having at least two olefinic double bonds;
   the proportions by weight being defined with respect to the total weight of the polymer.

Various other objects, features and attendant advantages of the present invention will be more fully appreciated as the same becomes better understood from the following detailed description.

DETAILED DESCRIPTION OF THE INVENTION

In a preferred embodiment of the invention, the oily phase of the triple emulsion contains at least one silicone oil.

This emulsion can advantageously be used as vehicle for a water-sensitive and/or oxygen-sensitive active agent, in particular as topical composition, in particular a cosmetic and/or dermatological composition. For a topical application, the emulsion according to the invention must contain a topically acceptable medium, that is to say compatible with the skin, mucous membranes and keratinous fibers, such as the hair.

The triple emulsion according to the invention has the advantage of being stable while preserving the activity of the active agents. The active agent is preferably contained in the inner aqueous phase of the triple emulsion, from where it is released during the application of the composition to the skin, mucous membranes or hair.

The emulsifying copolymers which can be used in the emulsion according to the present invention are prepared by polymerizing a predominant amount of a monoolefinically unsaturated carboxylic acid monomer or of its anhydride with a smaller amount of acrylic ester monomer with a fatty chain. Fatty chain is understood to mean a linear or branched alkyl radical comprising from 8 to 30 carbon atoms, inclusive of all specific values and subranges therebetween.

The amount of carboxylic acid monomer or of its anhydride preferably ranges from 80 to 98% by weight and more particularly from 90 to 98% by weight, whereas the acrylic ester monomer is present in amounts ranging from 2 to 20% by weight and more particularly from 1 to 10% by weight, the percentages being calculated with respect to the weight of the two monomers.

The preferred carboxylic acid monomers are chosen from those corresponding to the following formula (I):

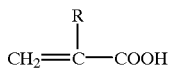
(I)

where R denotes hydrogen, a halogen, a hydroxyl group, a lactone group, a lactam group, a cyanogen group (—C≡N), a monovalent alkyl group, an aryl group, an alkylaryl group, an aralkyl group or a cycloaliphatic group.

The particularly preferred carboxylic acid monomers are chosen from acrylic acid, methacrylic acid or their mixtures.

The acrylic ester monomers with a fatty chain are preferably chosen from those corresponding to the following formula (II):

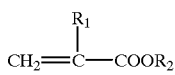
(II)

where $R_1$ is hydrogen, a methyl radical and or ethyl radical, and $R_2$ is a $C_8$–$C_{30}$ alkyl radical.

The particularly preferred ester monomers are those in which $R_1$ is hydrogen or a methyl radical and $R_2$ is a $C_{10}$–$C_{22}$ alkyl radical.

The emulsifying copolymers can optionally be crosslinked using a crosslinking agent used in an amount ranging from 0.1 to 4%, preferably from 0.2 to 10%, by weight with respect to the total weight of carboxylic acid monomers and of acrylic ester monomers. The crosslinking agent is chosen from polymerizable monomers comprising a polymerizable $CH_2$=C— group and at least one other polymerizable group, the unsaturated bonds of which are not conjugated with respect to one another.

The emulsifying copolymers of the invention are disclosed in patent application EP-A-0,268,164, incorporated herein by reference, and are obtained according to the preparation methods disclosed therein.

The particularly preferred emulsifying copolymers are those exhibiting a viscosity, measured with a Brookfield viscometer in a 2% solution in water at 25° C., of less than or equal to 5000 cPs (5 Pa·s) and more preferably of the order of approximately 3000 cPs (3 Pa·s).

Use is more particularly made of an acrylate/$C_{10}$–$C_{30}$ alkyl acrylate copolymer and in particular that sold under the name Pemulen TR 1 by Goodrich.

The emulsifying copolymer is used in the triple emulsion according to the invention in a concentration ranging, for example, from 0.05 to 3% and preferably from 0.1 to 1% and better still from 0.2 to 0.8% of the total weight of the emulsion.

The crosslinked poly(2-acrylamido-2-methylpropanesulfonic acid)s used according to the invention are water-soluble polymers or polymers which can swell in water.

The polymers used according to the invention preferably comprise a number of units of formula (III) in an amount which is sufficiently high to produce a hydrodynamic volume of the polymer in solution in water having a radius ranging from 10 to 500 nm, with a homogeneous and unimodal distribution.

The more particularly preferred crosslinked poly(2-acrylamido-2-methylpropanesulfonic acid)s comprise from 98 to 99.5% by weight of units of formula (III) and from 0.2 to 2% by weight of the crosslinking units.

In the formula (III), $X^+$ represents a cation or a mixture of cations chosen in particular from a proton, an alkali metal cation, a cation equivalent to that of an alkaline earth metal or the ammonium ion.

The crosslinked poly(2-acrylamido-2-methylpropanesulfonic acid)s used according to the invention are preferably neutralized to at least 90%, that is to say that at most 10 mol % of the $X^+$ cations in the formula (III) are protons $H^+$.

More particularly, 90 to 100 mol % of the cations are $NH_4^+$ cations and 0 to 10 mol % are protons $H^+$.

The crosslinking monomers having at least two olefinic double bonds are chosen, for example, from dipropylene glycol diallyl ether, polyglycol diallyl ethers, triethylene glycol divinyl ether, hydroquinone diallyl ether, tetraallyloxethanoyl or other allyl or vinyl ethers polyfunctional alcohols, tetraethylene glycol diacrylate, triallylamine, trimethylolpropane diallyl ether, methylenebisacrylamide or divinylbenzene.

The crosslinking monomers having at least two olefinic double bonds are more particularly chosen from those corresponding to the following general formula (IV):

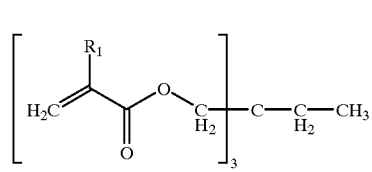
(IV)

in which $R_1$ denotes a hydrogen atom or a $C_1$–$C_4$ alkyl radical and more particularly a methyl radical. The preferred crosslinking agent is trimethylolpropane triacrylate.

The polymerization reaction of the poly(2-acrylamido-2-methylpropanesulfonic acid)s of the invention produces not only linear chains but also branched or crosslinked molecules of polymer. These molecules can be characterized in particular by their rheological behavior in water but more particularly by dynamic light scattering.

In the case of the characterization of the molecules by dynamic light scattering, the distribution of the hydrodynamic volume of the structures of the polymer is measured. Macromolecules dissolved in water are flexible and surrounded by a solvation envelope formed from water molecules. With charged polymers, such as those of the invention, the size of the molecules depends on the amount of salt in the water. In polar solvents, the uniform charge along the main chain of the polymer results in a significant expansion of the polymeric chain. The fact of increasing the amount of salt increases the amount of electrolyte in the solvent and screens the uniform charges of the polymer. In addition to the molecules transported in the solvation envelope, solvent molecules are fixed in the cavities of the polymer. In this case, the solvent molecules form part of the dissolved macromolecules and move at the same average speed. Thus, the hydrodynamic volume describes the linear dimension of the macromolecule and of these solvation molecules.

The hydrodynamic volume $v_h$ is determined by the following formula:

$$V_h = M/N_A \times (V_2 + dV_1)$$

where:

M is the mass in grams of the undissolved macromolecule;

$N_A$ is Avogadro's number;

$V_1$ is the specific volume of the solvent;

$V_2$ is the specific volume of the macromolecule;

d is the mass in grams of the solvent which is associated with 1 gram of undissolved macromolecule.

If the hydrodynamic particle is spherical, it is then easy to calculate the hydrodynamic radius from the hydrodynamic volume by the formula:

$$V_h = 4\pi R^3/3$$

where R is the hydrodynamic radius.

Cases where hydrodynamic particles are perfect spheres are extremely rare. The majority of synthetic polymers involve compacted structures or ellipsoids of high eccentricity. In this case, the radius is determined with respect to a sphere which is equivalent from a frictional viewpoint to the shape of the particle under consideration.

As a general rule, the determination is carried out with respect to distributions of molecular weight and thus with respect to distributions of hydrodynamic radius and volume. For polydispersed systems, it is necessary to calculate the distribution of the diffusion coefficients. From this distribution, the results relating to the radial distribution and to the distribution of the hydrodynamic volumes are deduced therefrom.

The hydrodynamic volumes of the polymers of the invention are in particular determined by dynamic light scattering from the Stokes-Einstein diffusion coefficients D of formula: $D = kT/6\pi\eta R$ where k is Boltzmann's constant, T is the absolute temperature in degrees Kelvin, $\eta$ is the viscosity of the solvent (water), and R is the hydrodynamic radius.

These diffusion coefficients D are measured according to the method of characterization of a mixture of polymers by laser scattering described in the following references, all of which are incorporated herein by reference:

(1) Pecora, R; Dynamic Light Scattering; Plenium Press, New York, 1976;

(2) Chu, B; Dynamic Light Scattering; Academic Press, New York, 1994;

(3) Schmitz, K S; Introduction to Dynamic Light Scattering; Academic Press, New York, 1990;

(4) Provincher S. W.; Comp. Phys., 27, 213, 1982;

(5) Provincher S. W.; Comp. Phys., 27, 229, 1982;

(6) ALV Laservertriebgesellschaft mbH, Robert Bosch Str. 47, D-63225 Langen, Germany;

(7) ELS-Reinheimer Strasse 11, D-64846 Gross-Zimrnem, Germany;

(8) Chi Wu et al., Macromolecules, 1995, 28, 4914–4919.

The particularly preferred crosslinked poly(2-acrylamido-2-methylpropanesulfonic acid)s are those exhibiting a viscosity, measured on a Brookfield viscometer, rotor 4, at a rotational speed of 100 revolutions/minute in a 2% solution in water at 25° C., of greater than or equal to 1000 cPs (1 Pa·s) and more preferably ranging from 5000 to 40,000 cPs (5 Pa·s to 40 Pa·s) and more particularly from 6500 to 35,000 cPs (6.5 Pa·s to 35 Pa·s).

The crosslinked poly(2-acrylamido-2-methylpropanesulfonic acid)s of the invention can be obtained according to the preparation process comprising the following stages:

(a) the 2-acrylamido-2-methylpropanesulfonic acid (AMPS) monomer is dispersed or dissolved in the free form in a tert-butanol or water and tert-butanol solution;

(b) the solution or the dispersion of AMPS monomer obtained in (a) is neutralized with one or more inorganic or organic bases, preferably ammonia $NH_3$, in an amount which makes it possible to obtain a degree of neutralization of the sulfonic acid functional groups of the polymer ranging from 90 to 100%;

(c) the crosslinking monomer or monomers is/are added to the solution or dispersion obtained in (b);

(d) a conventional radical polymerization is carried out in the presence of free radical initiators at a temperature ranging from 10 to 150° C., the polymer precipitating in the solution or dispersion based on tert-butanol.

The crosslinked poly(2-acrylamido-2-methylpropanesulfonic acid) is present in the triple emulsion according to the invention in a concentration ranging, for example, from 0.01 to 10%, preferably from 0.5 to 2.5% and better still from 1.5 to 2.5% of the total weight of the composition. According to a specific embodiment of the invention, the poly(2-acrylamido-2-methylpropanesulfonic acid) is incorporated in the triple emulsion in two steps, in order to facilitate the preparation thereof.

In the triple emulsion according to the invention, the primary emulsion is a W/O emulsion, the oily phase of which is advantageously composed essentially of at least one silicone-comprising emulsifier and/or one silicone oil.

The silicone-comprising emulsifiers used in the triple emulsion of the invention can be chosen from dimethicone copolyols and alkyl dimethicone copolyols. Mention may be made, as emulsifier which can be used in the emulsion according to the invention, of the polyglyceryl-4 isostearate/cetyl dimethicone copolyol/hexyl laurate mixture sold under the name "Abil WE 09" by Goldschmidt, the cetyl dimethicone copolyol sold under the name "Abil EM 90" by the company Goldschmidt and the cyclomethicone/dimethicone copolyol mixture sold under the name "Q2-3225C" by Dow Corning. Other silicone-containing emulsifiers suitable for the present invention are described in the International Cosmetic Ingredient Dictionary and Handbook (CTFA), Volume 2, Seventh Edition, p. 1594–1595, incorporated herein by reference.

The amount of silicone-comprising emulsifier in the emulsion according to the invention ranges, for example, from 0.01 to 10% and preferably from 0.05 to 5% of the total weight of the triple emulsion.

The silicone oils can be chosen, for example, from volatile silicones, such as cyclopentadimethyl-siloxane and cyclotetradimethylsiloxane, polydimethylsiloxanes, polyphenyltrimethylsiloxanes or fluorinated silicones. The amount of silicone oils ranges from 0.5 to 40% and preferably from 2 to 30% of the total weight of the triple emulsion.

The primary emulsion of the invention can, in addition, comprise one or more other fatty substances chosen from waxes, silicone gums and silicone resins and optionally oils other than silicone oils, such as oils of plant origin (apricot kernel oil) or synthetic oils (hydrogenated isoparaffin). These fatty substances can be used, for example, in an amount ranging from 0.05 to 10% and preferably from 0.5 to 5% of the total weight of the triple emulsion.

Use may in particular be made, as waxes, of silicone waxes, such as alkoxydimethylsiloxanes, and more particularly stearoxypolydimethylsiloxanes, alkylpolysiloxanes and polydimethylsiloxanes with a mercapto functional group.

Use may in particular be made, as gums, of silicone gums, such as high molecular weight polydimethylsiloxanes, or polydimethylsiloxanes with a hydroxyl ending (dimethiconols).

Use may in particular be made, as resins, of silicone resins, such as trimethylsiloxysilicates.

Mention may in particular be made, as oils other than silicone oils, of fluorinated oils, oils of animal or plant origin, mineral oils or synthetic oils.

The primary emulsion can represent, for example, from 10 to 40% and preferably from 20 to 30% of the total weight of the triple emulsion.

The triple emulsion is prepared conventionally by preparation of the primary emulsion and incorporation of a predetermined amount of the primary emulsion in the outer aqueous phase.

According to a specific embodiment of the invention, the primary emulsion contains a portion of the silicone oil, for example at most 20% by weight with respect to the total weight of the primary emulsion, and the remaining silicone oil is subsequently added to the amount of primary emulsion used to prepare the triple emulsion, before adding the mixture to the outer aqueous phase.

As indicated at the beginning of the description, one of the major advantages of the emulsion in accordance with the invention is that the latter can contain, while exhibiting a stable nature, active agents, both cosmetic and therapeutic active agents, in particular water-sensitive and/or oxygen-sensitive active agents and also active agents with an acidic nature, it being possible for these active agents thus to be chosen in particular from all those commonly used currently in the field of cosmetics, dermatology or medicaments.

Mention may in particular be made, as water-sensitive and/or oxygen-sensitive active agents, of enzymes (for example lactoperoxidase, lipase, protease, phospholipase or cellulases), natural extracts, such as green tea, balm extract or thyme extract, procyanidol oligomers (PCO), such as hawthorn PCO, pine PCO and grape PCO, vitamins and in particular ascorbic acid (vitamin C) and its esters, retinol (vitamin A) and its esters, phosphate-comprising and glucosylated derivatives, urea and rutin.

In addition to the abovementioned ascorbic acid, mention may also be made, inter alia, as active agents with an acidic nature, of kojic acid, caffeic acid, β-hydroxy acids, such as salicylic acid and its derivatives, α-hydroxy acids or α-ceto acids, such as lactic acid, methyllactic acid, citric acid, mandelic acid, glucuronic acid, glycolic acid, pyruvic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxytetraecosanoic acid, 2-hydroxyeicosanoic acid, benzilic acid, phenyllactic acid, gluconic acid, galacturonic acid, aleuritic acid, ribonic acid, tartronic acid, tartaric acid, malic acid, fumaric acid, retinoic acid and its derivatives, benzene-1,4-di(3-methylidene-10-camphorsulfonic acid) and their mixtures. It can also be any natural or synthetic compound comprising such acids, in particular plant extracts and, more especially, fruit extracts.

According to a specific embodiment of the invention, the triple emulsion of the invention comprises, as active agents, ascorbic acid and retinol, alone or as a mixture.

The active agent or the active agents can, for example, be present in a concentration ranging from 0.01 to 20%, preferably from 0.1 to 10% and better still from 0.5 to 5% of the total weight of the emulsion.

According to a specific embodiment of the invention, the primary emulsion comprises one or more polyols in an amount sufficient to lower the water activity of the inner phase of the triple emulsion, in order to stabilize water-sensitive active agents, such as ascorbic acid. The water activity of the primary emulsion advantageously ranges from 0.5 to 0.8. The polyols can, for example, be chosen from glycerol, glycols, such as propylene glycol and PEG 8, and silicones comprising hydroxyl groups. The polyols can be present in an amount preferably ranging from 0.5 to 50% and preferably from 25 to 45% of the total weight of the primary emulsion.

As indicated above, the W/O/W emulsions according to the invention can be used in various topical applications, in particular cosmetic and/or dermatological applications. The composition based on this emulsion can constitute in particular compositions for cleaning, protecting, treating or caring for the skin and/or the hair, in particular for the face, for the neck, for the hands, for the hair, for the scalp and for the body, as well as for the eyelashes.

A further subject-matter of the invention is consequently the cosmetic use of the composition according to the invention for cleaning and/or treating and/or protecting the skin and/or mucous membranes and/or keratinous fibers, that is to say the hair and/or the eyelashes.

Another subject-matter of the invention is the use of the composition according to the invention for the preparation of a dermatological composition intended for cleaning and/or treating and/or protecting the skin and/or mucous membranes and/or keratinous fibers, that is to say the hair and/or the eyelashes.

Another subject-matter of the invention is a cosmetic and/or dermatological process for cleaning and/or treating and/or protecting the skin and/or mucous membranes and/or keratinous fibers, characterized in that it consists in applying a composition as defined above to the skin, mucous membranes and/or keratinous fibers.

The composition according to the invention can constitute in particular creams for protecting, treating or caring for the face, for the hands or for the feet, protective or care body milks, or lotions, gels or foams for caring for the skin, mucous membranes, hair and scalp.

In a known way, the composition of the invention can also comprise adjuvants usual in the cosmetic and dermatological fields, such as surfactants, in particular foaming surfactants, hydrophilic or lipophilic active agents other than the active agents indicated above, preservatives, antioxidants, sequestering agents, solvents, fragrances, fillers, screening agents, odor absorbers and coloring materials. The amounts of these various adjuvants are those conventionally used in the fields under consideration, for example from 0.01% to 15% of the total weight of the composition. They can also comprise lipid vesicles formed from ionic or nonionic lipids.

These adjuvants, depending on their nature, can be introduced into the fatty phase or into the aqueous phase.

Use may be made, as hydrophilic active agents, in addition to the polyols indicated above, of, for example, proteins or protein hydrolysates, amino acids, allantoin, sugars and sugar derivatives, or starch.

Use may be made, as lipophilic active agents, of, for example, tocopherol (vitamin E) and its derivatives, essential fatty acids, ceramides or essential oils.

Having generally described this invention, a further understanding can be obtained by reference to certain specific examples which are provided herein for purposes of illustration only and are not intended to be limiting unless otherwise specified.

EXAMPLES

Example of preparation of a crosslinked poly(2-acrylamido-2-methylpropanesulfonic acid) neutralized with ammonia 2006.2 g of tert-butanol are introduced into a 5 liter round-bottomed flask equipped with a stirrer, a reflux condenser, a thermometer and a conveying device for nitrogen and for ammonia, followed by 340.0 g of 2-acrylamido-2-methylpropanesulfonic acid, which is dispersed in the solution with vigorous stirring. After 30 minutes, ammonia is added via the upper pipe of the round-bottomed flask and the reaction mixture is kept at room temperature for 30 minutes until a pH of the order of 6–6.5 is obtained. 32.0 g of a 25% solution of trimethylolpropane triacrylate in tert-butanol are subsequently introduced and the reaction mixture is heated to 60° C. while simultaneously being rendered inert by introducing nitrogen into the round-bottomed flask. Once this temperature has been reached, dilauroyl peroxide is added. The reaction begins immnediately, which is reflected by a rise in temperature and by a precipitation of the polymerizate. Fifteen minutes after the beginning of the polymerization, a stream of nitrogen is introduced. Thirty minutes after the addition of the initiator, the temperature of the reaction mixture reaches a maximum of 65–70° C. Thirty minutes after having reached this temperature, the reaction mixture is heated to reflux and is maintained under these conditions for 2 hours. The formation of a thick paste is observed during the reaction. The reaction mixture is cooled to room temperature and the product obtained is filtered off. The recovered paste is subsequently dried under vacuum at 60–70° C. for 24 hours. 391 g of crosslinked and neutralized poly(2-acrylamido-2-methylpropanesulfonic acid) are obtained with a viscosity, measured on a Brookfield viscometer, rotor 4, at a rotational speed of 100 revolutions/minute in a 2% solution in water at 25° C., ranging from 15,000 cPs to 35,000 cPs (15 Pa·s to 35 Pa·s). The viscosity of the polymer will be chosen and controlled according to conventional means depending on the cosmetic application envisaged.

The hydrodynamic radius of the polymer obtained in an aqueous solution, determined by dynamic light scattering, is 440 nm.

Example 1
Moisturizing emulsion for a radiant complexion

1. Primary emulsion:

Phase A:

| | |
|---|---|
| Abil WE 09 | 2.5% |
| Volatile silicone oil | 17.5% |
| Polydimethylsiloxane | 4% |

Phase B:

| | |
|---|---|
| Glycerol | 39% |
| Ascorbic acid | 15% |
| Sequestering agent | 0.1% |
| Preservative | 0.8% |
| Demineralized water | 21.1% |

2. Triple emulsion:

Phase A:

| | |
|---|---|
| Primary emulsion | 20% |
| Silicone oil | 10% |

Phase B:

| | |
|---|---|
| Crosslinked poly(2-acrylamido-2-methylpropanesulfonic acid) neutralized with ammonia, prepared according to the process of the preparation example (viscosity of the order of 16 Pa · s in a 2% solution in water at 25° C.) | 0.5% |
| Acrylate/$C_{10}$–$C_{30}$ alkyl acrylate copolymer (Pemulen TR1) | 0.3% |
| Preservatives | 1% |
| Demineralized water | 40% |

Phase C:

| | |
|---|---|
| Triethanolamine | 0.3% |
| Demineralized water | 2% |

Phase D:

| | |
|---|---|
| Crosslinked poly(2-acrylamido-2-methylpropanesulfonic acid) neutralized with ammonia, prepared according to the process of the preparation example (viscosity of the order of 16 Pa · s in a 2% solution in water at 25° C.) | 1.5% |
| Demineralized water | 24.4% |

The triple emulsion is prepared in the following way:

1. The primary emulsion is prepared by mixing the constituents of the phase A at room temperature, by furthermore mixing the constituents of the phase B at room temperature and by slowly pouring the phase B into the phase A with rapid stirring.
2. To prepare the triple emulsion, the various phases are prepared and then the phase A is slowly poured into the phase B with rapid stirring. The phase C is added thereto and then the phase D. Stirring is carried out until the mixture is completely homogeneous.

Example 2
A composition analogous to that of Example 1 can be prepared by replacing ascorbic acid with glycolic acid.

Example 3
Emulsion for smoothing the skin

Primary emulsion:

Phase A:

| | |
|---|---|
| Abil WE 09 | 2.5% |
| Volatile silicone oil | 17.5% |
| Polydimethylsiloxane | 4% |

Phase B:

| | |
|---|---|
| Glycerol | 45% |
| Ascorbic acid | 10% |
| Preservative | 0.8% |
| Demineralized water | 20.2% |

2. Triple emulsion:

Phase A:

| | |
|---|---|
| Primary emulsion | 20% |
| Volatile silicone oil | 10% |

Phase B:

| | |
|---|---|
| Crosslinked poly(2-acrylamido-2-methylpropanesulfonic acid) neutralized with ammonia, prepared according to the process of the preparation example (viscosity of the order of 16 Pa · s in a 2% solution in water at 25° C.) | 0.5% |
| Acrylate/$C_{10}$–$C_{30}$ alkyl acrylate copolymer (Pemulen TR1) | 0.3% |
| Preservatives | 1% |
| Demineralized water | 40% |

Phase C:

| | |
|---|---|
| Triethanolamine | 0.3% |
| Demineralized water | 2% |

Phase D:

| | |
|---|---|
| Crosslinked poly(2-acrylamido-2-methylpropanesulfonic acid) neutralized with ammonia, prepared according to the process of the preparation example (viscosity of the order of 16 Pa · s in a 2% solution in water at 25° C.) | 1.5% |
| Demineralized water | 24.4% |

The triple emulsion is prepared according to the same procedure as for Example 1.

A white cream is obtained which is capable of smoothing the skin.

Example 4
Care emulsion

1. Primary emulsion:

Phase A:

| | |
|---|---|
| Abil WE 09 | 3.5% |
| Hydrogenated isoparaffin | 23% |

Phase B:

| | |
|---|---|
| Glycerol | 39% |
| Preservative | 1% |
| Demineralized water | 33.7% |

2. Triple emulsion:

Phase A:

| | |
|---|---|
| Primary emulsion | 20% |
| Hydrogenated isoparaffin | 4% |
| Apricot kernel oil | 5% |
| Retinol | 0.1% |
| BHT (antioxidant) | 0.11% |

Phase B:

| | |
|---|---|
| Crosslinked poly(2-acrylamido-2-methylpropanesulfonic acid) neutralized with ammonia, prepared according to the process of the preparation example (viscosity of the order of 16 Pa · s in a 2% solution in water at 25° C.) | 1% |
| Acrylate/$C_{10}$–$C_{30}$ alkyl acrylate copolymer (Pemulen TR1) | 0.6% |
| Preservative | 1% |
| Demineralized water | 64.09% |

Phase C:

| | |
|---|---|
| Triethanolamine | 1.1% |
| Demineralized water | 3% |

The triple emulsion is prepared according to the same procedure as for Example 1. A white cream is obtained which is capable of smoothing the skin.

Example 5
Care emulsion

1. Primary emulsion:

Phase A:

| | |
|---|---|
| Abil WE 09 | 3.5% |
| Hydrogenated isoparaffin | 20.5% |

Phase B:

| | |
|---|---|
| Glycerol | 39% |
| Preservative | 0.8% |
| Ascorbic acid | 15% |
| Demineralized water | 21.2% |

2. Triple emulsion:

Phase A:

| | |
|---|---|
| Primary emulsion | 20% |
| Hydrogenated isoparaffin | 4% |
| Apricot kernel oil | 5% |
| Retinol | 0.1% |
| Lipocarnosine | 0.1% |

Phase B:

| | |
|---|---|
| Crosslinked poly(2-acrylamido-2-methylpropanesulfonic acid) neutralized with ammonia, prepared according to the process of the preparation example (viscosity of the order of 16 Pa · s in a 2% solution in water at 25° C.) | 1% |
| Acrylate/$C_{10}$–$C_{30}$ alkyl acrylate copolymer (Pemulen TR1) | 0.6% |
| Preservative | 1% |
| Demineralized water | 64.1% |

Phase C:

| | |
|---|---|
| Triethanolamine | 1.1% |
| Demineralized water | 3% |

The triple emulsion is prepared according to the same procedure as for Example 1. A white cream is obtained which is capable of smoothing the skin and of improving the radiance of the complexion Stability test: The following test is intended to demonstrate the superiority of the claimed combination of gelling agents with respect to other combinations. The example according to the invention is Example 1. In the comparative example, the crosslinked poly(2-acrylamido-2-methylpropanesulfonic acid) is replaced by Carbopol 980. The characteristics of the triple emulsion obtained are given in the following table:

| Polymer | Example 1 according to the invention | Comparative example |
|---|---|---|
| Poly(2-acrylamido-2-methylpropanesulfonic acid) of the preparation example | X | |
| Acrylate/$C_{10}$–$C_{30}$ alkyl acrylate copolymer (Pemulen TR1) | X | |
| Acrylate/$C_{10}$–$C_{30}$ alkyl acrylate copolymer (Carbopol 1382) | | X |
| Carbopol 980 (1) | | X |
| Formation of a triple emulsion | Yes | Yes |
| Stability after 24 hours | Stable | Unstable |

(1) Carbopol 980: carboxyvinyl polymer

This table shows that only the combination according to the invention makes it possible to obtain a stable triple emulsion in the presence of an acidic compound.

Obviously, numerous modifications and variations of the present invention are possible in light of the above teachings. It is therefore to be understood that within the scope of the appended claims, the invention may be practiced otherwise than as specifically described herein.

French Patent Application 97-12364, filed on Oct. 3, 1997, is incorporated herein by reference in its entirety.

What is claimed is:

1. A water/oil/water triple emulsion, comprising:

an inner aqueous phase emulsified in an oily phase; and a gelled outer aqueous phase, wherein the oily phase comprises an emulsifier selected from the group consisting of alkyl dimethicone copolyols and dimethicone copolyols, and the outer aqueous phase comprises:
(1) at least one emulsifying copolymer composed to a major extent of a polymerized monoolefinically unsaturated $C_3$–$C_6$ carboxylic acid monomer or of an anhydride thereof and to a minor extent of an acrylic acid fatty ester monomer, and
(2) at least one crosslinked poly(acrylamidomethylpropanesulfonic acid) comprising, distributed randomly:
(a) from 90 to 99.9% by weight of units represented by formula (III):

$$\begin{array}{c} \text{H}_2 \\ \diagup \text{C} \diagdown \\ \text{CH} \\ | \\ \text{O}=\text{C} \\ | \\ \text{N}-\overset{\text{CH}_3}{\underset{\text{CH}_3}{\text{C}}}-\text{CH}_2\text{SO}_3^-\text{X}^+ \\ \text{H} \end{array} \quad (\text{III})$$

wherein $X^+$ is a cation or a mixture of cations, (b) from 0.01 to 10% by weight of crosslinking units derived from at least one monomer having at least two olefinic double bonds;

wherein the percentages of by weight of (a) and (b) are with respect to the total weight of the crosslinked poly(acrylamidomethyl-propanesulfonic acid).

2. The emulsion of claim 1, wherein the amount of carboxylic acid monomer or the anhydride thereof in the emulsifying copolymer is from 80 to 98% by weight and the amount of acrylic ester monomer is from 20 to 2% by weight, wherein the percentages by weight are with respect to the total weight of the carboxylic acid monomer and the acrylic ester monomer.

3. The emulsion of claim 1, wherein carboxylic acid monomer is a compound represented by formula (I):

$$\text{CH}_2=\overset{\text{R}}{\underset{}{\text{C}}}-\text{COOH} \quad (\text{I})$$

wherein R is hydrogen, a halogen, a hydroxyl group, a lactone group, a lactam group, a cyanogen group, a monovalent alkyl group, an aryl group, an alkylaryl group, an aralkyl group or a cycloaliphatic group, and the ester monomer is a compound represented by formula (II):

$$\text{CH}_2=\overset{\text{R}_1}{\underset{}{\text{C}}}-\text{COOR}_2 \quad (\text{II})$$

wherein $R_1$ is hydrogen, a methyl radical or an ethyl radical; and
$R_2$ is a $C_8$–$C_{30}$ alkyl group.

4. The emulsion of claim 3, wherein the carboxylic acid monomer is selected from the group consisting of acrylic acid, methacrylic acid and mixtures thereof; and the ester monomer is selected from the group consisting of monomers of formula (II) in which $R_1$ is hydrogen or a methyl radical and $R_2$ is a $C_{10}$–$C_{22}$ alkyl group.

5. The emulsion of claim 1, wherein the emulsifying copolymer comprises from 0.05 to 3% of the total weight of the emulsion.

6. The emulsion of claim 1, wherein the crosslinked poly(2-acrylamido-2-methylpropanesulfonic acid) comprises from 98 to 99.5% by weight of the units represented formula (III) and from 0.2 to 2% by weight of the crosslinking units.

7. The emulsion of claim 1, wherein the crosslinked poly(2-acrylamido-2-methylpropanesulfonic acid) is neutralized to at least 90%.

8. The emulsion of claim 1, wherein $X^+$ is $NH_4^+$.

9. The emulsion of claim 1, wherein the crosslinking monomers are represented by the formula (IV):

$$\left[ \text{H}_2\text{C}=\overset{\text{R}_1}{\underset{}{\text{C}}}-\overset{\text{O}}{\underset{}{\text{C}}}-\text{O}-\text{C}\text{H}_2 \right]_3 \text{C}-\overset{}{\underset{\text{H}_2}{\text{C}}}-\text{CH}_3 \quad (\text{IV})$$

wherein $R_1$ is a hydrogen atom or a $C_1$–$C_4$ alkyl.

10. The emulsion of claim 1, wherein the poly(2-acrylamido-2-methylpropanesulfonic acid) is crosslinked by trimethylolpropane triacrylate.

11. The emulsion of claim 1, wherein the crosslinked poly(2-acrylamido-2-methylpropanesulfonic acid) has a viscosity, as measured on a Brookfield viscometer, rotor 4, at a rotational speed of 100 revolutions/minute in a 2% solution in water at 25° C., of greater than or equal to 1 Pa·s.

12. The emulsion of claim 1, wherein the crosslinked poly(2-acrylamido-2-methylpropanesulfonic acid) comprises from 0.01 to 10% of the total weight of the emulsion.

13. The emulsion of claim 1, wherein the oily phase comprises at least one silicone oil in an amount ranging from 0.5 to 40% of the total weight of the emulsion.

14. The emulsion of claim 13, wherein the silicone oil is selected from the group consisting of volatile silicones, polydimethylsiloxanes, polyphenyltrimethylsiloxanes and fluorinated silicones.

15. The emulsion of claim 1, wherein the emulsifying agent is present in an amount ranging from 0.01 to 10% of the total weight of the emulsion.

16. The emulsion of claim 1, wherein the oily phase additionally contains one or more other fatty substances selected from the group consisting of waxes, silicone gums, silicone resins, fluorinated oils, oils of animal origin, oils of plant origin, mineral oils and synthetic oils.

17. The emulsion of claim 1, wherein the inner aqueous phase emulsified in the oily phase comprises from 10 to 40% of the total weight of the emulsion.

18. The emulsion of claim 1, wherein the inner aqueous phase emulsified in the oily phase comprises contains at least one polyol.

19. The emulsion of claim 1, wherein in that the polyol comprise from 0.5 to 50% of the weight of the inner aqueous phase emulsified in the oily phase.

20. A topical composition, comprising the emulsion of claim 1 and at least one active agent.

21. The composition of claim 20, wherein the active agent is selected from the group consisting of water-sensitive and/or oxygen-sensitive active agents and acidic active agents.

22. The composition of claim 20, wherein the active agent is selected from the group consisting of enzymes, natural extracts, procyanidol oligomers, vitamins, phosphate-comprising and glucosylated derivatives, urea, rutin, kojic acid, caffeic acid, β-hydroxy acids, α-hydroxy acids, retinoic acid and its derivatives, benzene-1,4-di(3-methylidene-10-camphorsulfonic acid), plant extracts comprising such an acid, and mixtures thereof.

23. The composition of claim 20, wherein the active agent is ascorbic acid, retinol, salicylic acid, lactic acid, methyllactic acid, citric acid, mandelic acid, glucuronic acid, glycolic acid, pyruvic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxytetraecosanoic acid, 2-hydroxyeicosanoic acid, benzilic acid, phenyllactic acid, gluconic acid, galacturonic acid, aleuritic acid, ribonic acid, tartronic acid, tartaric acid, malic acid, fumaric acid, their derivatives or a mixture thereof.

24. The composition of claim 20, comprising, as active agents, ascorbic acid and retinol.

25. The composition of claim 20, wherein the active agents comprises from 0.01 to 20% of the total weight of the composition.

26. The composition of claim 20, further comprising at least one lipophilic or hydrophilic adjuvant selected from the group consisting of preservatives, antioxidants, sequestering agents, solvents, fragrances, fillers, screening agents, odor absorbers, coloring materials, hydrophilic or lipophilic active agents and lipid vesicles.

27. A method of cleaning and/or treating and/or protecting the skin and/or mucous membranes and/or keratinous fibers, comprising applying an effective amount of the composition of claim 20 to skin and/or mucous membranes and/or keratinous fibers.

28. A method of making the composition of claim 20, comprising combining emulsion and the active agent.

* * * * *